US012565905B2

(12) United States Patent
Lemieux et al.

(10) Patent No.: US 12,565,905 B2
(45) Date of Patent: Mar. 3, 2026

(54) QUICK CONNECT FOR ROBOTIC SURGICAL INSTRUMENTS

(71) Applicant: Orthosoft ULC, Montreal (CA)

(72) Inventors: Marc-André Lemieux, Montreal (CA); Brian Edward Roach, Osceola, IN (US)

(73) Assignee: Orthosoft ULC, Montreal (CA)

( * ) Notice: Subject to any disclaimer, the term of this patent is extended or adjusted under 35 U.S.C. 154(b) by 886 days.

(21) Appl. No.: 17/747,635

(22) Filed: May 18, 2022

(65) Prior Publication Data

US 2022/0395343 A1 Dec. 15, 2022

Related U.S. Application Data

(60) Provisional application No. 63/210,285, filed on Jun. 14, 2021.

(51) Int. Cl.
| *F16B 9/00* | (2006.01) |
| *A61B 17/00* | (2006.01) |
| *A61B 34/30* | (2016.01) |
| *F16B 2/18* | (2006.01) |

(52) U.S. Cl.
CPC .............. *F16B 9/058* (2018.08); *F16B 2/185* (2013.01); *A61B 2017/00464* (2013.01); *A61B 2034/305* (2016.02); *Y10T 403/1624* (2015.01); *Y10T 403/53* (2015.01)

(58) Field of Classification Search
CPC ...... A61B 2034/305; A61B 2017/0046; A61B 2017/00464; F16B 2/185; F16B 7/042; F16B 9/058; F16B 21/165; Y10S 403/04; Y10T 403/1616; Y10T 403/1624; Y10T 403/53; Y10T 403/535; Y10T 403/7182; Y10T 403/7188

USPC .................................................. 403/235, 236
See application file for complete search history.

(56) References Cited

U.S. PATENT DOCUMENTS

| 125,539 | A | | 4/1872 | Callen | |
| 2,696,649 | A | | 12/1954 | Clapper | |
| 4,573,717 | A | | 3/1986 | Peacock | |
| 4,705,305 | A | | 11/1987 | Ghaly | |
| 5,193,930 | A | * | 3/1993 | Chi | B62K 21/12 |
| | | | | | 403/191 |
| 5,479,836 | A | | 1/1996 | Chang | |

(Continued)

FOREIGN PATENT DOCUMENTS

| EP | 2194906 B1 | 3/2015 |
| EP | 3565509 B1 | 5/2024 |

(Continued)

OTHER PUBLICATIONS

"U.S. Appl. No. 15/647,605, Corrected Notice of Allowability mailed Apr. 19, 2019", 10 pgs.

(Continued)

*Primary Examiner* — Amber R Anderson
*Assistant Examiner* — Kevin J Baynes
(74) *Attorney, Agent, or Firm* — SCHWEGMAN LUNDBERG & WOESSNER, P.A.

(57) ABSTRACT

A coupler can connect one or more instruments to a robotic surgical arm. The coupler can include a base and an actuator. The base can be securable to the robotic surgical arm. The actuator can be operable to release or secure the stem to the base and the robotic surgical arm.

16 Claims, 10 Drawing Sheets

(56) References Cited

U.S. PATENT DOCUMENTS

| | | | | |
|---|---|---|---|---|
| 6,214,057 | B1 * | 4/2001 | Spencer | B25J 19/063 |
| | | | | 403/41 |
| 6,231,565 | B1 * | 5/2001 | Tovey | A61B 34/30 |
| | | | | 606/1 |
| 6,299,180 | B1 * | 10/2001 | Satran | B23B 31/1076 |
| | | | | 408/233 |
| 6,394,998 | B1 * | 5/2002 | Wallace | A61B 34/35 |
| | | | | 901/29 |
| 6,458,163 | B1 * | 10/2002 | Slemker | A61F 2/76 |
| | | | | 623/38 |
| 6,474,747 | B2 * | 11/2002 | Beaulieu | F16B 7/042 |
| | | | | 30/296.1 |
| 6,689,171 | B2 * | 2/2004 | Slemker | A61F 2/78 |
| | | | | 623/33 |
| 7,473,234 | B1 | 1/2009 | Weltner et al. | |
| 8,268,011 | B2 | 9/2012 | Newcombe et al. | |
| 8,457,790 | B2 * | 6/2013 | Blondel | A61B 34/77 |
| | | | | 700/254 |
| 8,668,402 | B2 * | 3/2014 | Mori | F16L 41/12 |
| | | | | 403/175 |
| 9,782,224 | B2 * | 10/2017 | Piccin | B25J 15/12 |
| 9,933,097 | B2 * | 4/2018 | Buttolph | F42B 15/36 |
| 10,076,844 | B2 * | 9/2018 | Rizk | B25J 15/0491 |
| 10,369,026 | B2 | 8/2019 | Toler | |
| 10,772,745 | B2 | 9/2020 | Porter et al. | |
| 11,533,999 | B2 * | 12/2022 | Saperton | F16B 2/185 |
| 11,547,523 | B2 * | 1/2023 | Roussel | A61B 90/57 |
| 11,578,746 | B2 * | 2/2023 | Stuut | E04B 1/585 |
| 11,752,015 | B2 | 9/2023 | Porter et al. | |
| 2002/0149123 | A1 | 10/2002 | Edel et al. | |
| 2003/0036748 | A1 * | 2/2003 | Cooper | A61B 34/30 |
| | | | | 901/29 |
| 2004/0267254 | A1 * | 12/2004 | Manzo | A61B 18/14 |
| | | | | 606/49 |
| 2005/0049720 | A1 | 3/2005 | Benson | |
| 2008/0086150 | A1 * | 4/2008 | Mathis | A61B 34/20 |
| | | | | 606/130 |
| 2008/0219760 | A1 * | 9/2008 | Wu | F16B 2/185 |
| | | | | 403/322.4 |
| 2008/0288087 | A1 | 11/2008 | Bachus et al. | |
| 2011/0190907 | A1 | 8/2011 | Porter et al. | |
| 2015/0164659 | A1 | 6/2015 | Konishi | |
| 2015/0257904 | A1 | 9/2015 | Brnemark et al. | |
| 2018/0014951 | A1 | 1/2018 | Toler | |
| 2018/0125597 | A1 * | 5/2018 | Gogarty | A61B 34/30 |
| 2018/0185174 | A1 | 7/2018 | Porter et al. | |
| 2020/0368042 | A1 | 11/2020 | Porter et al. | |
| 2021/0015578 | A1 | 1/2021 | Marchese | |

FOREIGN PATENT DOCUMENTS

| | | |
|---|---|---|
| NL | 2010991 C | 12/2014 |
| WO | WO-2007018904 A2 | 2/2007 |
| WO | WO-2013141777 A1 | 9/2013 |
| WO | WO-2018128903 A1 | 7/2018 |
| WO | WO-2019177569 A1 | 9/2019 |
| WO | WO-2021005177 A1 | 1/2021 |

OTHER PUBLICATIONS

"U.S. Appl. No. 15/647,605, Notice of Allowance mailed Feb. 20, 2019", 13 pgs.

"U.S. Appl. No. 15/647,605, Response filed Jan. 31, 2019 to Restriction Requirement mailed Dec. 18, 2018", 7 pgs.

"U.S. Appl. No. 15/647,605, Restriction Requirement mailed Dec. 18, 2018", 7 pgs.

"U.S. Appl. No. 15/856,566, Advisory Action mailed Apr. 17, 2020", 4 pgs.

"U.S. Appl. No. 15/856,566, Corrected Notice of Allowability mailed Aug. 20, 2020", 2 pgs.

"U.S. Appl. No. 15/856,566, Final Office Action mailed Jan. 30, 2020", 13 pgs.

"U.S. Appl. No. 15/856,566, Non Final Office Action mailed Sep. 20, 2019", 9 pgs.

"U.S. Appl. No. 15/856,566, Notice of Allowance mailed May 12, 2020", 5 pgs.

"U.S. Appl. No. 15/856,566, Response filed Mar. 30, 2020 to Final Office Action mailed Jan. 30, 2020", 12 pgs.

"U.S. Appl. No. 15/856,566, Response filed Apr. 30, 2020 to Advisory Action mailed Apr. 17, 2020", 12 pgs.

"U.S. Appl. No. 15/856,566, Response filed Dec. 18, 2019 to Non Final Office Action mailed Sep. 20, 2019", 11 pgs.

"U.S. Appl. No. 16/991,601, Preliminary Amendment filed Sep. 8, 2020", 6 pgs.

"European Application Serial No. 17832703.7, Communication Pursuant to Article 94(3) EPC mailed Mar. 24, 2021", 5 pgs.

"European Application Serial No. 17832703.7, Communication Pursuant to Article 94(3) EPC mailed Jun. 24, 2020", 5 pgs.

"European Application Serial No. 17832703.7, Response filed Sep. 16, 2021 to Communication Pursuant to Article 94(3) EPC mailed Mar. 24, 2021", 15 pgs.

"European Application Serial No. 17832703.7, Response filed Nov. 4, 2020 to Communication Pursuant to Article 94(3) EPC mailed Jun. 24, 2020", 17 pgs.

"European Application Serial No. 17832703.7, Response to Communication pursuant to Rules 161(1) and 162 EPC filed Feb. 21, 2020", 12 pgs.

"International Application Serial No. PCT/US2017/068696, International Preliminary Report on Patentability mailed Jul. 18, 2019", 7 pgs.

"International Application Serial No. PCT/US2017/068696, International Search Report mailed May 4, 2018", 4 pgs.

"International Application Serial No. PCT/US2017/068696, Written Opinion mailed May 4, 2018", 5 pgs.

"OPRA Implant System Product Catalouge", Intergrum AB, (accessed Apr. 17, 2018), 8 pgs.

U.S. Appl. No. 15/647,605 U.S. Pat. No. 10,369,026, filed Jul. 12, 2017, Clamping Quick Connect Mechanism for Axial Attachment.

U.S. Appl. No. 15/856,566 U.S. Pat. No. 10,772,745, filed Dec. 28, 2017, Failsafe Device for Prosthetic Limb.

U.S. Appl. No. 16/991,601, filed Aug. 12, 2020, Failsafe Device for Prosthetic Limb.

"U.S. Appl. No. 16/991,601, Corrected Notice of Allowability mailed May 17, 2023", 2 pgs.

"U.S. Appl. No. 16/991,601, Non Final Office Action mailed Oct. 26, 2022", 14 pgs.

"U.S. Appl. No. 16/991,601, Notice of Allowance mailed May 4, 2023", 9 pgs.

"U.S. Appl. No. 16/991,601, Response filed Jan. 25, 2023 to Non Final Office Action mailed Oct. 26, 2022", 13 pgs.

"Canadian Application Serial No. 3,160,358, Examiners Rule 86(2) Requisition mailed Aug. 11, 2023", 4 pgs.

"Canadian Application Serial No. 3,160,358, Response Filed Nov. 20, 2023 to Examiners Rule 86(2) Requisition mailed Aug. 11, 2023", 16 pgs.

"European Application Serial No. 22179062.9, Extended European Search Report mailed Nov. 10, 2022", 9 pgs.

"European Application Serial No. 22179062.9, Response filed Jun. 21, 2023 to Extended European Search Report mailed Nov. 10, 2022", 12 pgs.

* cited by examiner

QUICK CONNECT FOR ROBOTIC SURGICAL INSTRUMENTS

CLAIM OF PRIORITY

This application claims the benefit of U.S. Provisional Patent Application Ser. No. 63/210,285, filed on Jun. 14, 2021, the benefit of priority of which is claimed hereby, and which is incorporated by reference herein in its entirety.

BACKGROUND

The present disclosure relates generally to apparatus and devices used during robotically-assisted surgical procedures, such as for robotic joint replacement procedures, or arthroplasty procedures. Often, during a robotically-assisted surgical procedure, one or more tools are used during the procedure. The tools can be connected to the robotic surgical arm, allowing the robotic surgical arm to use or manipulate the tools during the procedure.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

In robotic surgical procedures, a variety of tools or instruments can be used. For example, a joint replacement procedure, or arthroplasty, can involve making an access incision in a region of a patient, such as a shoulder or a hip. Cutting instruments can then be used to ream or drill the bone, trial components can be used to size implants, and the implants can be secured to the bones using one or more fasteners. Various tools are used to perform these and other steps of the procedure. During such a surgery, instruments coupled to the robotic surgical arms are often changed at each step of the procedure to avoid use of many surgical arms. Changing of cutting tools of the end effector of the robotic surgical arm can add considerable time during a procedure where many changes are required. Additionally, instrument changes can impact accuracy and/or require timely recalibration of the robotic arm.

The present disclosure helps to address these issues by providing a coupling system having a quick connect mechanism. The coupler can include a base configured to receive a tool stem therein. The base can be secured the end effector to allow the coupler to quickly and easily secure stems of various tools to the base and therefore to the robotic surgical arm. Optionally, the coupler can include a collar that is movable to secure the tool stem to the surgical arm. The collar can be quickly actuated by an actuator to secure the stem and the tool to the arm. In this way, the coupler can help save significant time during tool changes during a procedure. The design of the coupler allows for accurately and repeatably positioning of different instruments with respect to the end effector and coordinate system maintained by the robotic system. Accurately and repeatably positioning of the various instruments assists in avoiding time consuming recalibration—further assisting in speeding up a robotically assisted surgical procedure.

The above discussion is intended to provide an overview of subject matter of the present patent application. It is not intended to provide an exclusive or exhaustive explanation of the invention. The description below is included to provide further information about the present patent application.

Figure 1A:
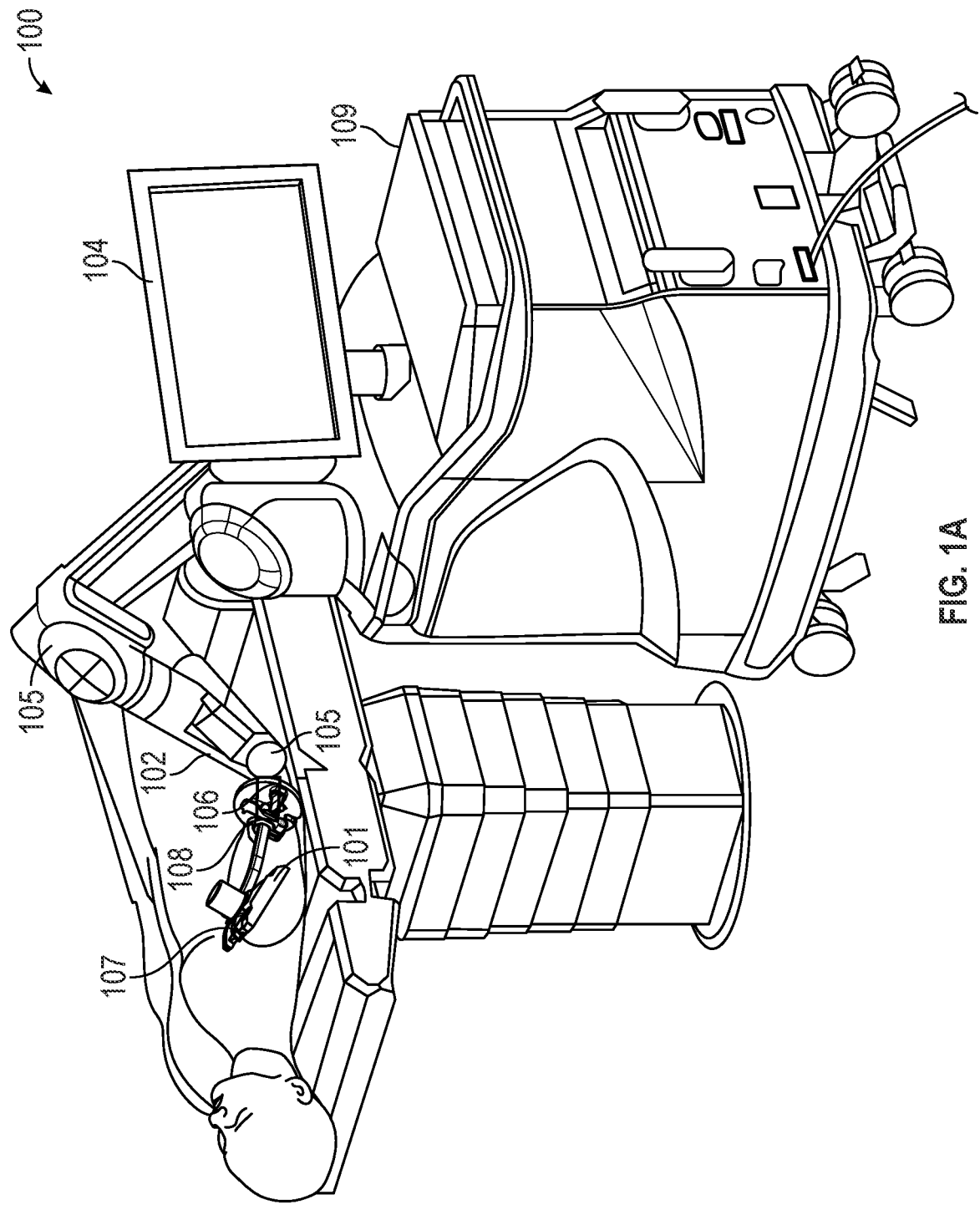
FIG. 1A illustrates a perspective view of a robotic surgical system.
Figure 1B:
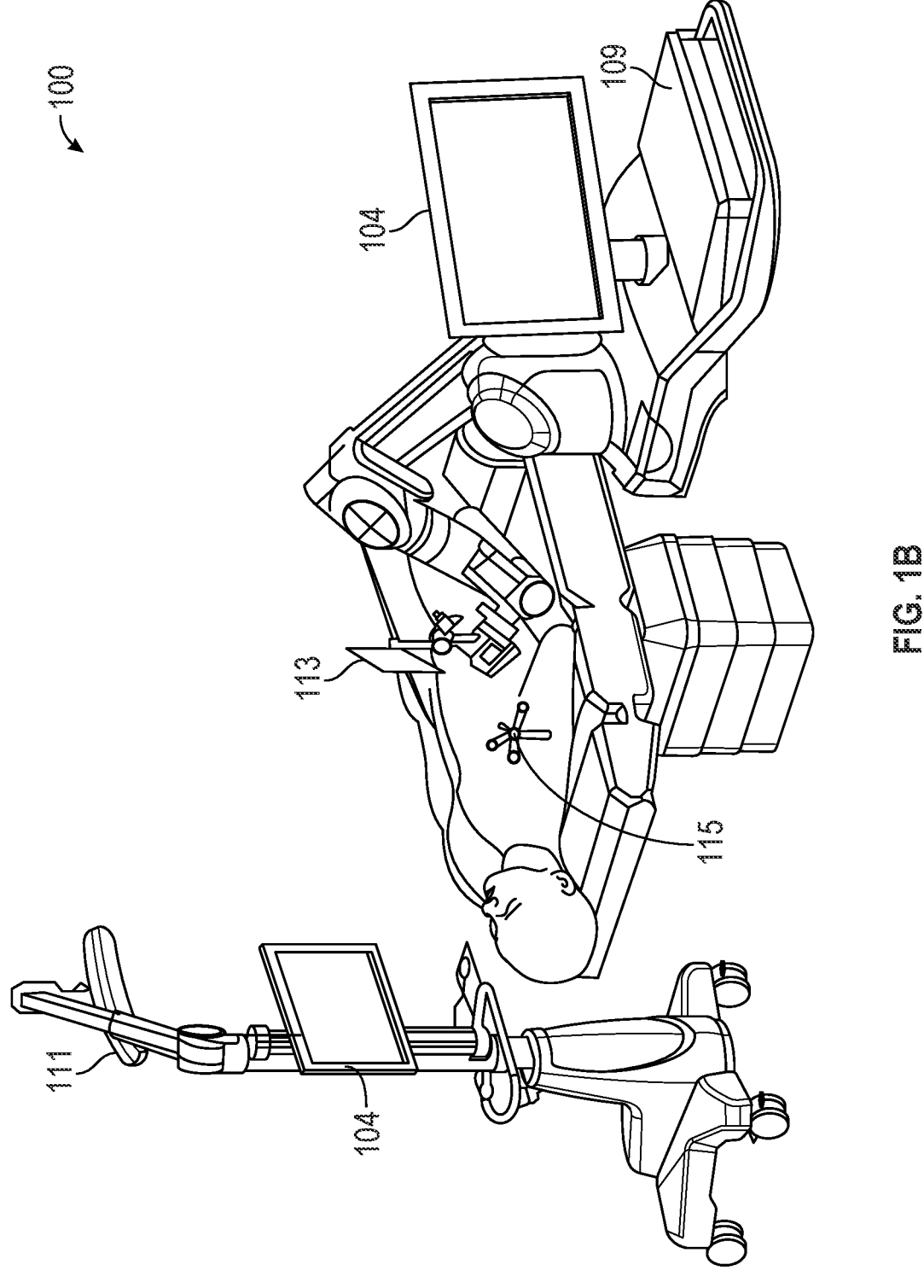
FIG. 1B illustrates a perspective view of a robotic surgical system.

FIG. 1A illustrates a perspective view of a robotic surgical system 100 including a coupler system 101 coupled to a robotic arm 102. FIG. 1B illustrates an isometric view of the robotic surgical system 100. FIGS. 1A and 1B are discussed together below.

The coupler system 101 can be used to secure instruments or tools to the robotic arm 102. The robotic arm 102 can be a 6 degree-of-freedom (DOF) robot arm, such as the ROSA® robot from Medtech, a Zimmer Biomet Holdings, Inc. company. The robotic arm 102 can be controlled by a surgeon with various control devices or systems. For example, a surgeon can use a control system (e.g., a controller that is processor-implemented based on machine-readable instructions, which when implemented cause the robotic arm to move automatically or to provide force assistance to surgeon-guided movement) to guide the robotic arm 102. The robotic arm 102 can include two or more articulating joints 105 capable of pivoting, rotating, or both, to provide a surgeon with wide range of adjustment options. A surgeon can also use anatomical imaging, such as displayed on a display screen 104, to guide and position the robotic arm 102. Anatomical imaging can be provided to the display screen 104 with various imaging sources, such as one or more cameras positioned on the coupler system 101, or intraoperative fluoroscopy, such as a C-arm.

The anatomical imaging, for example, can be imaging of internal patient anatomy within an incision 107. The incision 107 can be made in a variety of positions on a patient. For example, in a shoulder arthroplasty procedure, the incision 107 can be made in a shoulder region of a patient. The incision 107 can be configured to allow one or more tools coupled to the robotic arm 102 to access a bone surface, or other anatomy of the patient. The robotic arm 102 can include an end effector 106. The end effector 106 can include a base 108, which can be configured to couple the coupler system 101 to the robotic arm 102.

The robotic system 100 can include a computing system 109, which can also communicate with display screens 104 and a tracking system 111 (shown in FIG. 1B). The tracking system 111 can be operated by the computing system 109 as a stand-alone unit. The computing system 109 can optionally utilize the Polaris optical tracking system from Northern Digital, Inc. of Waterloo, Ontario, Canada. The tracking system 111 can monitor a plurality of tracking elements, such as tracking elements 113 (shown in FIG. 1B). The tracking elements 113 can be affixed to objects of interest, to track locations of multiple objects within a surgical field.

The tracking system 111 can function to create a virtual three-dimensional coordinate system within the surgical field for tracking patient anatomy, surgical instruments, or portions of the end effector 106 or robotic arm 102. Tracking elements 115 can be tracking frames including multiple IR reflective tracking spheres, or similar optically tracked marker devices. In one example, the tracking elements 115 can be placed on or adjacent one or more bones of patient. In other examples, the tracking elements 115 can be placed on the end effector 106 and/or an implant to accurately track positions within the virtual coordinate system. In each instance the tracking elements 115 can provide position data, such as a patient position, a bone position, a joint position, an implant position, a position of the robotic arm 102, or the like.

Figure 2:
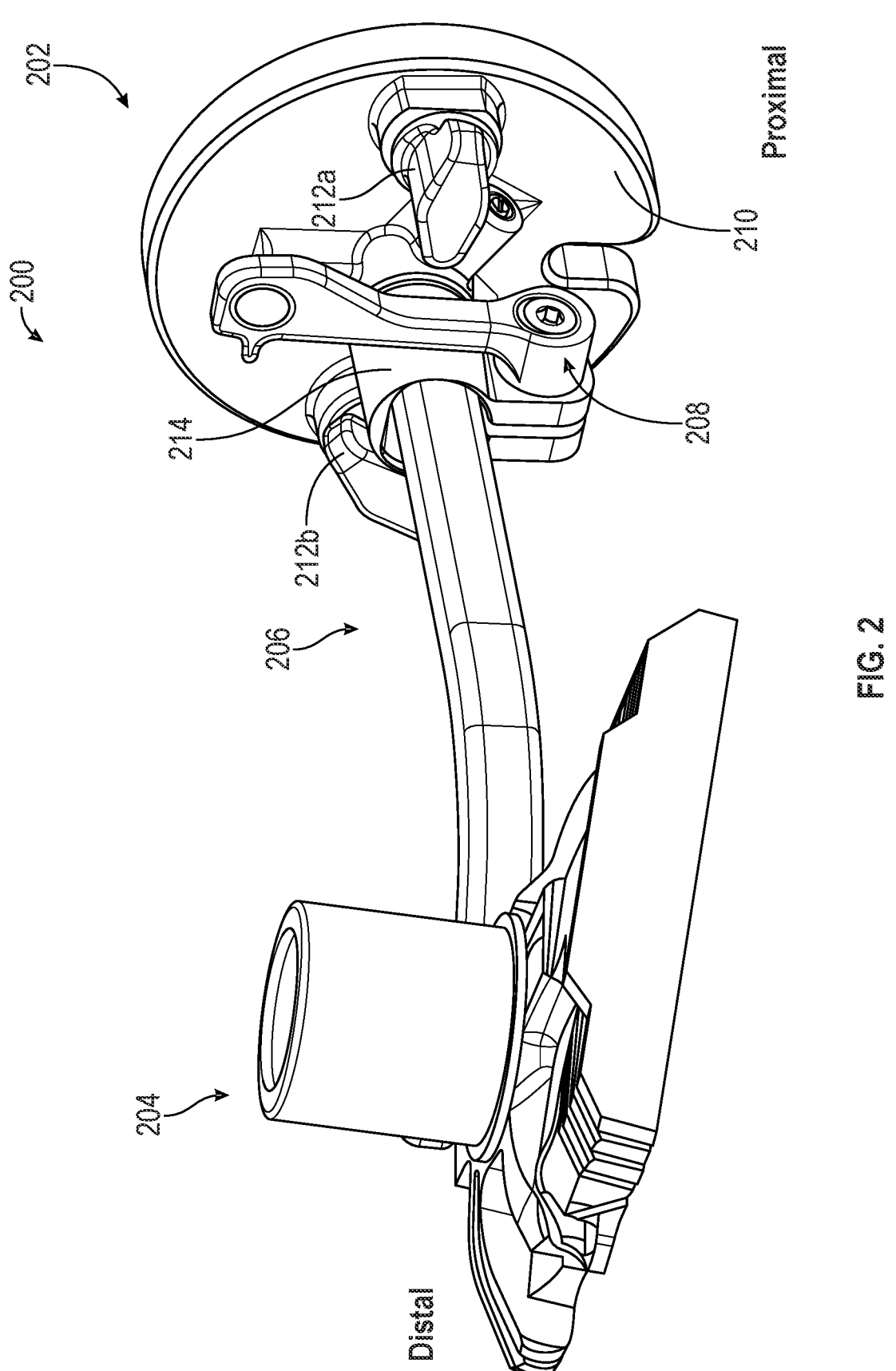
FIG. 2 illustrates an isometric view of a surgical tool and coupler for a robotic surgical system.

FIG. 2 illustrates an isometric view of a system 200 that can include a coupler 202 and a tool or instrument 204, which can include a stem 206. The tool or instrument 204 can be a reamer, a retractor, a trial component, a registration device, a cut guide, other standard surgical instruments, or the like.

The coupler 202 can include an actuator 208 and a base 210. The coupler 202 can also include fasteners 212a and 212b that can be configured to extend through the base 210 (and secured to the base 210) to secure the base 210 to a plate or base of an end effector (e.g., the end effector 106 of the surgical arm 102). The components of the coupler 202 can made of materials such as one or more of metals, plastics, foams, elastomers, ceramics, composites, combinations thereof, or the like.

A collar 214 of the base 210 can be configured to receive at least a portion of the stem 206 of the tool 204 therein. The actuator 208 can be connected to a collar 214 of the base 210 and the actuator 208 can be operable to open and close the collar 214. In operation of some examples, the stem 206 can be inserted into the collar 214, such as when the actuator 208 and collar 214 are in an open position. The actuator 208 can be operated (such as when the stem 206 is located in the collar 214) to close the collar 214 to secure the stem 206 and the instrument 204 to the coupler 202 (and therefore to the surgical arm). Further details of the system 200 are discussed below with respect to FIGS. 3-5.

Figure 3A:
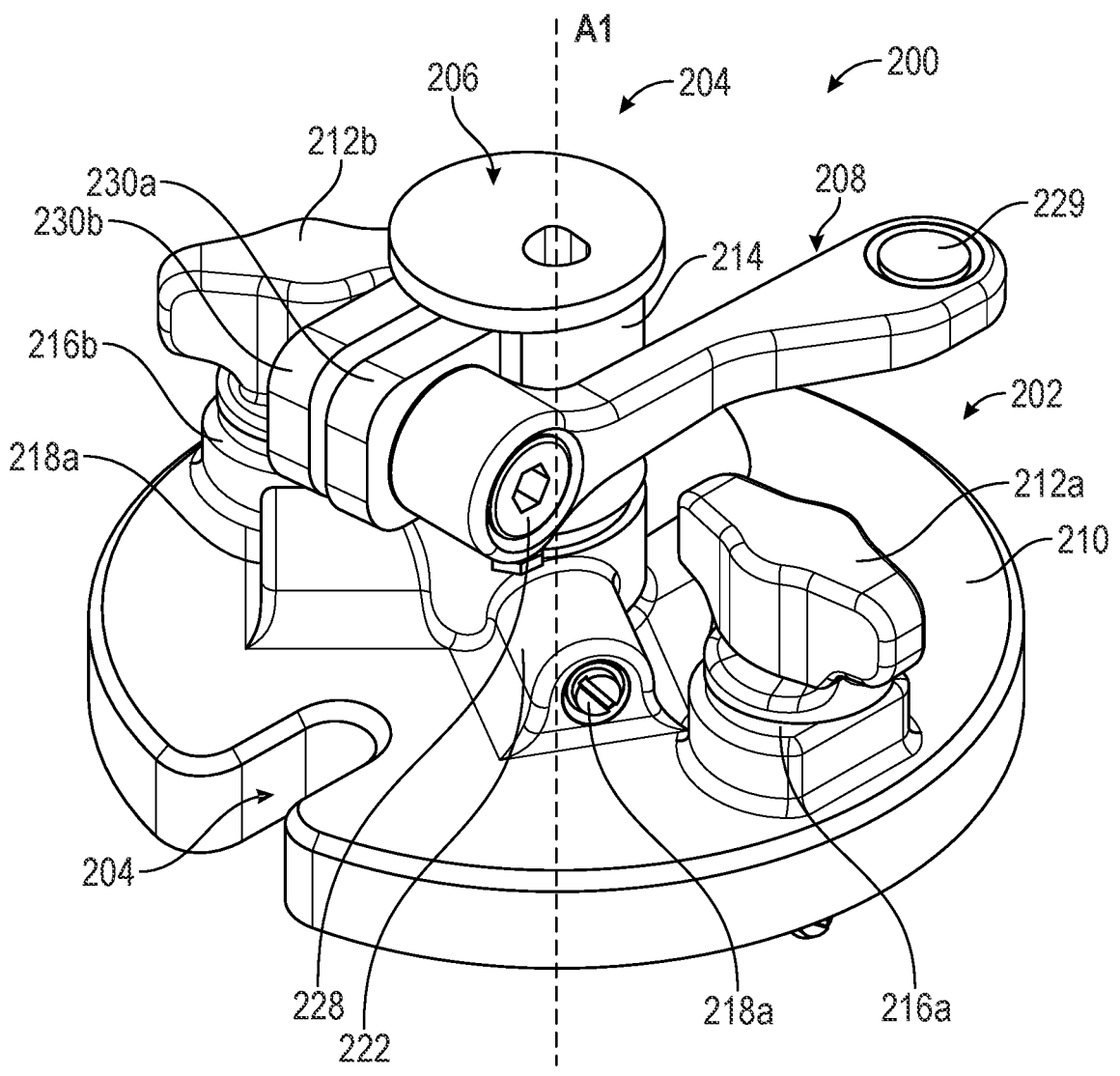
FIG. 3A illustrates an isometric view of a surgical tool and coupler for a robotic surgical system.
Figure 3B:
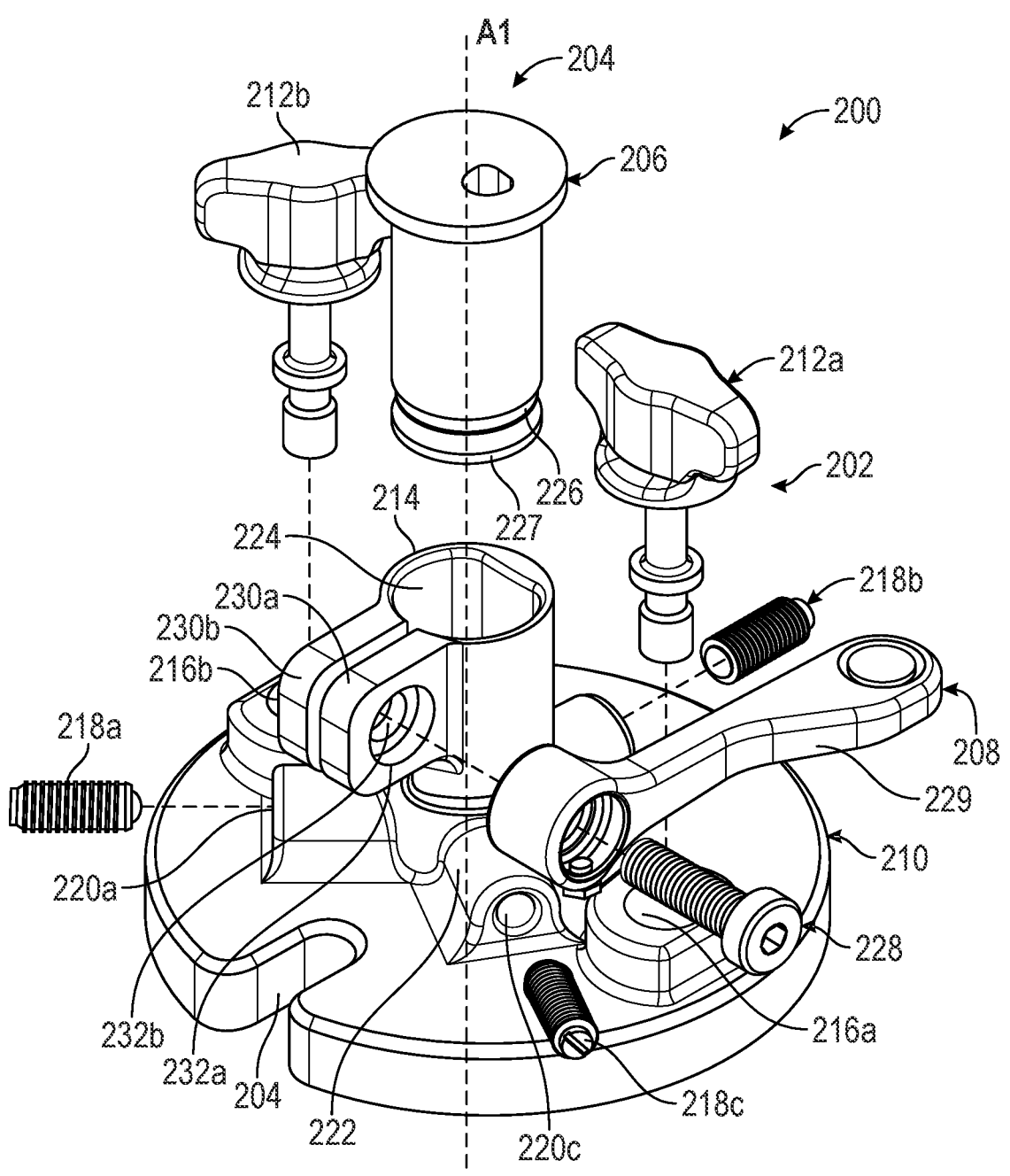
FIG. 3B illustrates an exploded isometric view of a surgical tool and coupler for a robotic surgical system.

FIG. 3A illustrates an isometric view of the surgical tool 204 and coupler 202. FIG. 3B illustrates an exploded isometric view of the surgical tool 204 and coupler 202. FIGS. 3A and 313 are discussed together below. The system 200 can be consistent with the system 200 of FIG. 2; further details are discussed with respect to FIGS. 3A and 3B.

For example, FIGS. 3A and 3B show that the fasteners 212a and 212b can be insertable into bores 216a and 216b of the base 210. The bores 216 can extend through the base 210 and can optionally be threaded to threadably engage the fasteners 212a and 212b to secure the base 210 to the end effector (e.g., 106) using the fasteners 212a and 212b.

FIGS. 3A and 3B also show retainers 218a-218c that can be insertable into bores 220a-220c, respectively, of the base 210. The bores 220a-220c can respectively extend through protrusions (e.g., 222) of the base 210, such that the base can at least partially define the bores 220a-220c. The bores 220a-220c can intersect a stem bore 224 of the collar 214 and can optionally be threaded to receive and secure the retainers 218a-218c therein. Each of the retainers 218a-218c can be inserted into their respective bore 220a-220c such that the retainers 218a-218c are configured to engage a groove 226 of the stem 206. The groove 226 can be a groove extending around at least a portion of a circumference or perimeter of the stem 206. Such engagement can limit axial movement (e.g., along the axis A1) of the stem 206 with respect to the collar 214 of the coupler 202.

The collar 214 can at least partially define the stem bore 224 that can extend at least partially into the base 210 such as along the axis A1. The stem bore 224 can be configured (e.g., sized and shaped) to receive at least a portion of the tool stem 206 therein. The collar 214 can also include a movable portion and a fixed portion (discussed below) where a first flange and a second flange are movable based on movement of the actuator 208 to secure the stem 206 to the collar 214 and to the base 210.

The stem 206 can also include a chamfered portion 227 at a proximal end of the stem 206. The chamfered portion 227 can engage the retainers 218 to cause the retainers 218 to move outward as the stem 206 is moved axially into the stem bore 224. The chamfered portion 227 can help to reduce friction between the retainers 218 and the stem 206 during insertion of the stem 206.

FIGS. 3A and 3B also show that the actuator 208 can include a handle 229 and a bolt 228. The actuator 208 can be connected to the collar 214 and can be operable to move the collar 214 between an open position and a closed position through engagement between the bolt 228 and flanges 230a and 230b of the collar 214. As shown in FIG. 3B, the flanges 230a and 230b can include bores 232a and 232b, respectively. The bore 232b can be threaded and the bore 232a can be configured to capture (or retain at least a portion of the bolt 228 therein.

In operation of some examples, operation (e.g., rotation) of the handle 229 can cause the bolt 228 to thread into the flange 230b, which can cause movement of the flange 230a with respect to the flange 230b. This movement of the flange 230a can cause the movable collar portion (of the collar 214) to move with respect to the fixed collar portion to cause the collar 214 to engage the stem 206 to secure the stem 206 to the base 210 and the robotic surgical arm. Further details and operations are discussed below with respect to FIGS. 4 and 5.

Figure 4:
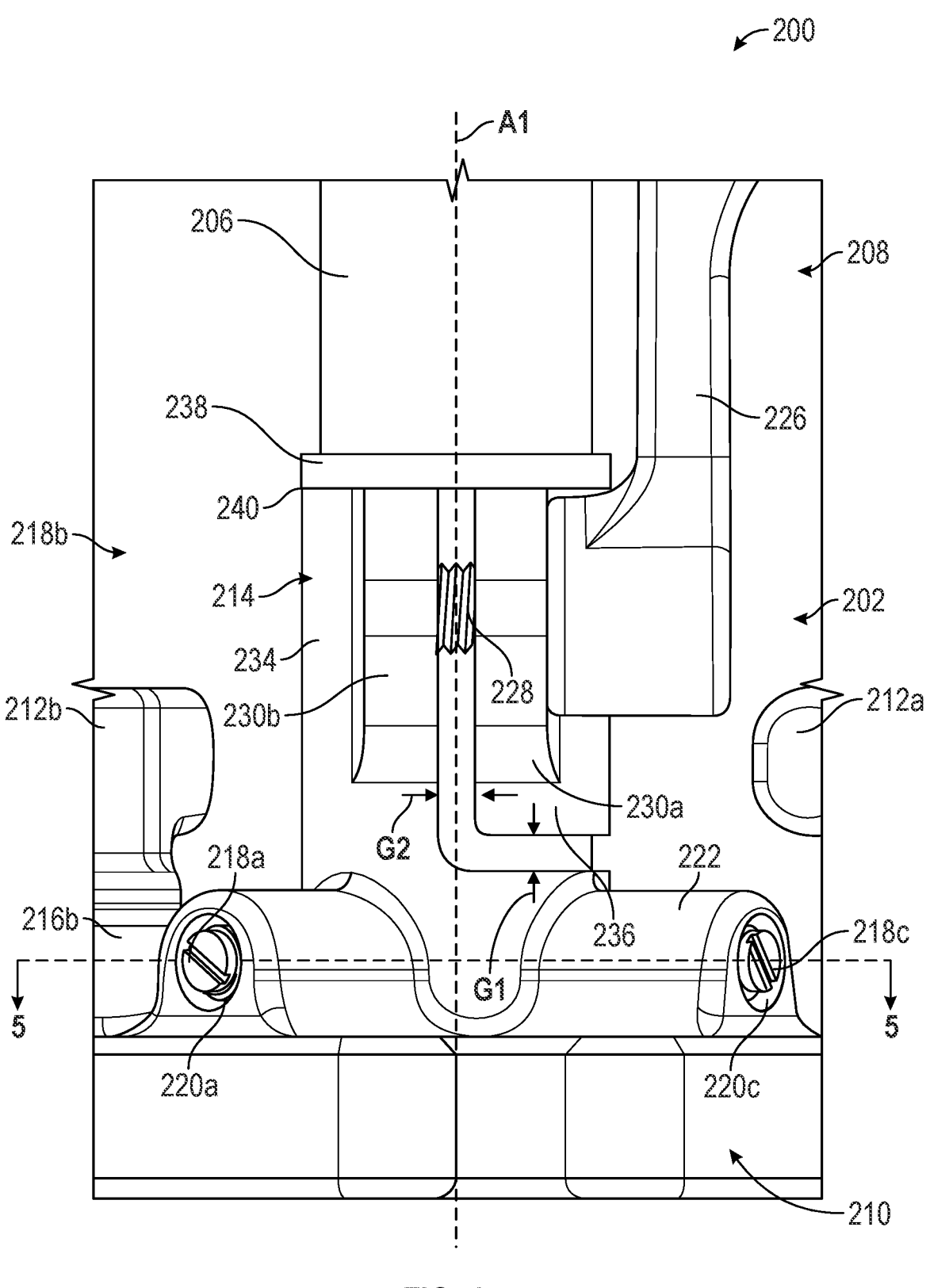
FIG. 4 illustrates a side view of a surgical tool and coupler for a robotic surgical system.

FIG. 4 illustrates a side view of the coupler 202 the robotic surgical system 200. The system 200 can be consistent with the system 200 of FIGS. 2-3B; further details are discussed with respect to FIG. 4. For example, FIG. 4 shows a fixed portion (or first portion) 234 and a movable portion (or second portion) 236 of the collar 214.

The fixed portion 234 can include the flange 230b and the movable portion 236 can include the flange 230a. The movable portion 236 can be cantilevered from the fixed portion such as to at least partially define a gap G1 between the movable portion 236 and the base 210 or a lower portion of the collar 214. The gap G1 can help allow for the movable portion 236 to move with respect to the fixed portion 234. The movable portion 236 can also be separated from the fixed portion 234 by the gap G2 which can be a distance that changes based on operation of the actuator 208. The gap G1 can extend around at least a quarter of a circumference or perimeter or periphery of the collar. In some examples, the gap G1 can extend around between 20% and 85% of the perimeter of the collar 214. In some examples, the gap G1 can extend around between 25% and 50% of the perimeter of the collar 214.

In operation of some examples, when the actuator 208 is operated to rotate in a first direction (e.g. counterclockwise from a right perspective with respect to FIG. 4), the bolt 228 can be (at least partially) unthreaded from the threaded bore 232*b* (of FIG. 3B) of the flange 230*b* to increase the gap G2 such that the stem 206 can be inserted into the stem bore 224 (shown in FIG. 3B) of the collar 214 (or removed from the collar 214, such as after use of the instrument 204). When the actuator 208 is operated to rotate in a second direction (e.g. clockwise from a right perspective with respect to FIG. 4), the bolt 228 can be (at least partially) threaded into the threaded bore 232*b* (shown in FIG. 3B) of the flange 230*b* to decrease the gap G2 such as to cause the collar 214 to clamp onto the stem 206 (when the stem 206 is within the bore 224). Such clamping or engagement of the collar 214 with the stem 206 can help limit non-axial movement of the stem 206 with respect to the collar 214, such as to help prevent accidental movement of the stem 206 with respect to the collar 214, the base 210, and the surgical arm. In this way, the stem 206 (and therefore the instrument 204) can be quickly, easily, and securely coupled to the coupler 202 and therefore to a robotic surgical arm.

By incorporating the gaps G1 and G2 to create the movable portion 236 and the fixed portion 234, only the movable portion 236 moves with respect to the base 210 in operation of the actuator 208. Such single-sided movement of the collar 214 (e.g., only the movable portion 236 moves) can help to provide predictable deformation or movement of collar 214. That is, by knowing which side of the collar 214 will bend, it can be more accurately predicted where a final position of the stem 206 will be with respect to the base 210 when the actuator 208 is operated to secure the stem 206 to the coupler 202. This increased accuracy in location predication can help to increase an accuracy of the robotic surgical system 100 that manipulates the tool 204 connected to the coupler 202, further helping to improve surgical accuracy.

FIG. 4 also shows the stem 206 can include a shoulder 238 that can be engageable with an end surface 240 of the collar 214 to limit axial movement of the stem 206 into the collar 214 and to provide a visual and tactile feedback to an operator of proper insertion. Such a feature can further help to accurately predict where a final position of the stem 206 will be with respect to the base 210 when the actuator 208 is operated to secure the stem 206 to the coupler 202, which can increase an accuracy of the robotic surgical system 100 that manipulates the tool 204 connected to the coupler 202.

Figure 5:
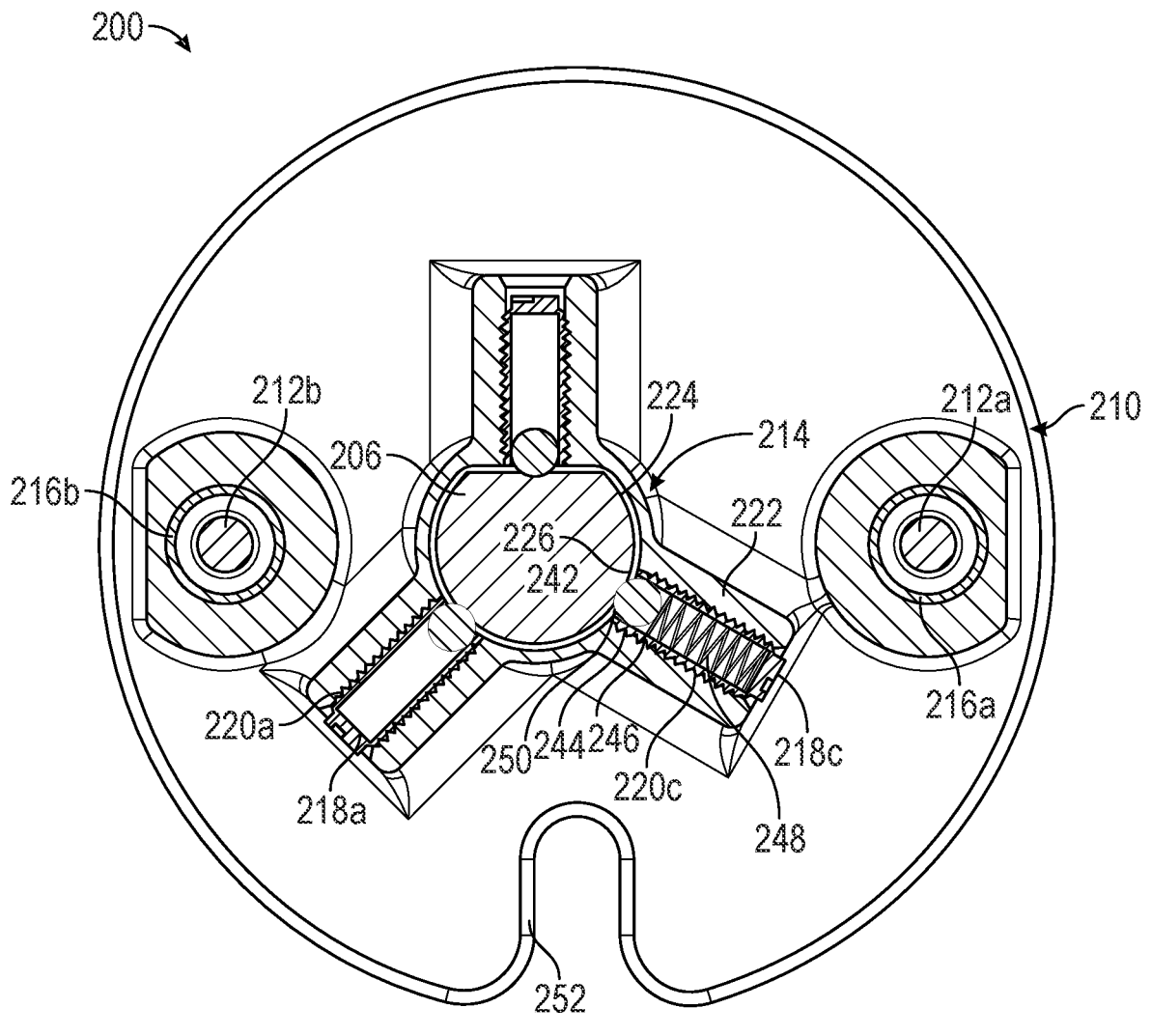
FIG. 5 illustrates a top cross-sectional view across indicators 5-5 of FIG. 4 of a surgical tool and coupler for a robotic surgical system.

FIG. 5 illustrates a top cross-sectional view across indicators 5-5 of FIG. 4 of the coupler 202 the robotic surgical system 200. The system 200 can be consistent with the system 200 of FIGS. 2-4; further details are discussed with respect to FIG. 5. For example, FIG. 5 shows how the retainers 218 interact with the stem 206.

The bores 220*a*-220*c* can be located with respect to the stem bore 224 of the collar 214 such that the retainer bore 220 each intersect the stem bore 224. When the retainers 218 are secured within the bores 220, respectively, a detent ball 242 of each retainer 218 can extend into the stem bore 224 to engage the recess 226 of the stem 206.

The retainers 218 can include a threaded portion 244 that can be engageable with the bores 220 (respectively) to threadably secure the retainers 218 to the bores 220 and to locate the retainers 218 properly with respect to the bore 224. The retainers 218 can also include an internal bore 246 that can house or retain a biasing element 248 (e.g., compression spring or the like). The biasing element 248 can engage the retainer 218 and the detent ball 242 to bias the ball 242 to extend from the internal bore 246.

Each bore 220 of the base 210 can also include a shoulder 250 engageable with a distal portion of the retainers 218, respectively, to position the retainers 218 (and therefore the detent balls 242) as desired with respect to the stem bore 224 such that the balls 242 can extend at least partially into the stem bore 224 and the groove or recess 226 of the stem 206 to help to retain the stem 206 within the bore 224.

FIG. 5 also shows that the stem bore 224 can have a D-shape cross section that is configured (e.g., sized or shaped) to receive the stem 206, which can have a complimentary D-shape, such that engagement between the stem bore 224 and the stem 206 can help limit relative rotation of the stem 206 with respect to the collar 214 and the base 210. The stem 206 and bore 224 can have other shapes to help limit relative rotation of the stem 206, such as an oval, a star shape, a rectangle, or the like.

FIG. 5 also shows that the base 210 can include a notch 252 that can extend at least partially into the base 210 from an outer perimeter of the base 210. Such a notch can be used to engage a feature of the end effector of a surgical arm to align the bores 216 with bores of the end effector and generally orient the base 210 and therefore coupler 202 and instrument 204 in a predetermined and known location.

Figure 6:
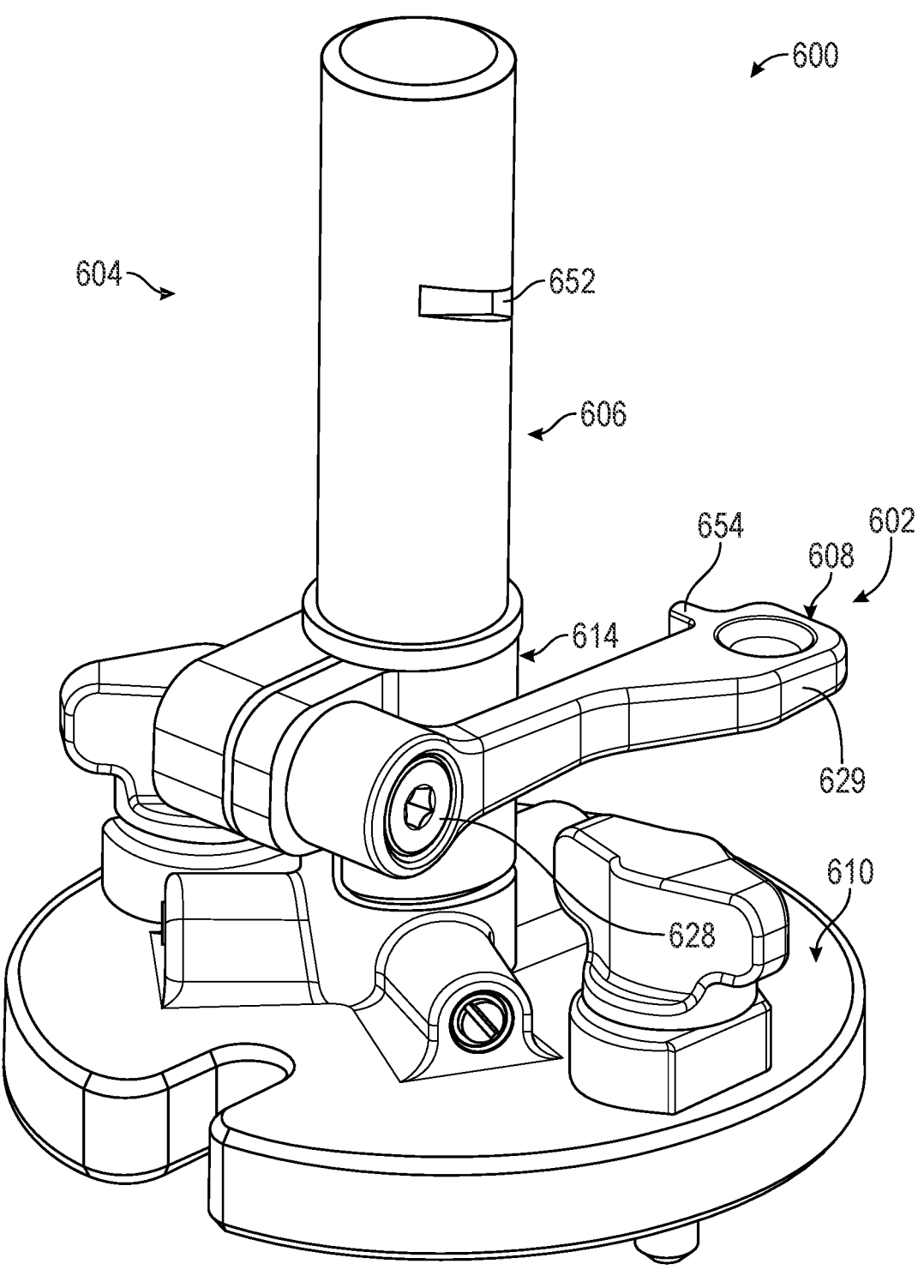
FIG. 6 illustrates an isometric view of a surgical tool and coupler for a robotic surgical system.

FIG. 6 illustrates an isometric view of a surgical tool 604 and coupler 602 for a robotic surgical system 600. The system 600 can be similar to the system 200 of FIGS. 2-5 where like numerals can represent like components; the system 600 can differ in that the stem and actuator can include interlocking features. Any of the systems or couplers discussed above or below can be modified to include such features.

More specifically, a stem 606 of the tool 604 can include a slot 652 or notch therein. The slot 652 can be configured to receive a projection 654 of a handle 629 of an actuator 608 such that when the actuator 608 is operated to turn or rotate a bolt 628 with respect to a base 610, the projection 654 can be positioned within the notch 652. When the stem 606 is inserted sufficiently into a collar 614 of the coupler 602, the projection 654 can be rotated insert into the slot 652, indicating that the stem 606 is properly axially oriented or located within the collar 614.

Figure 7:
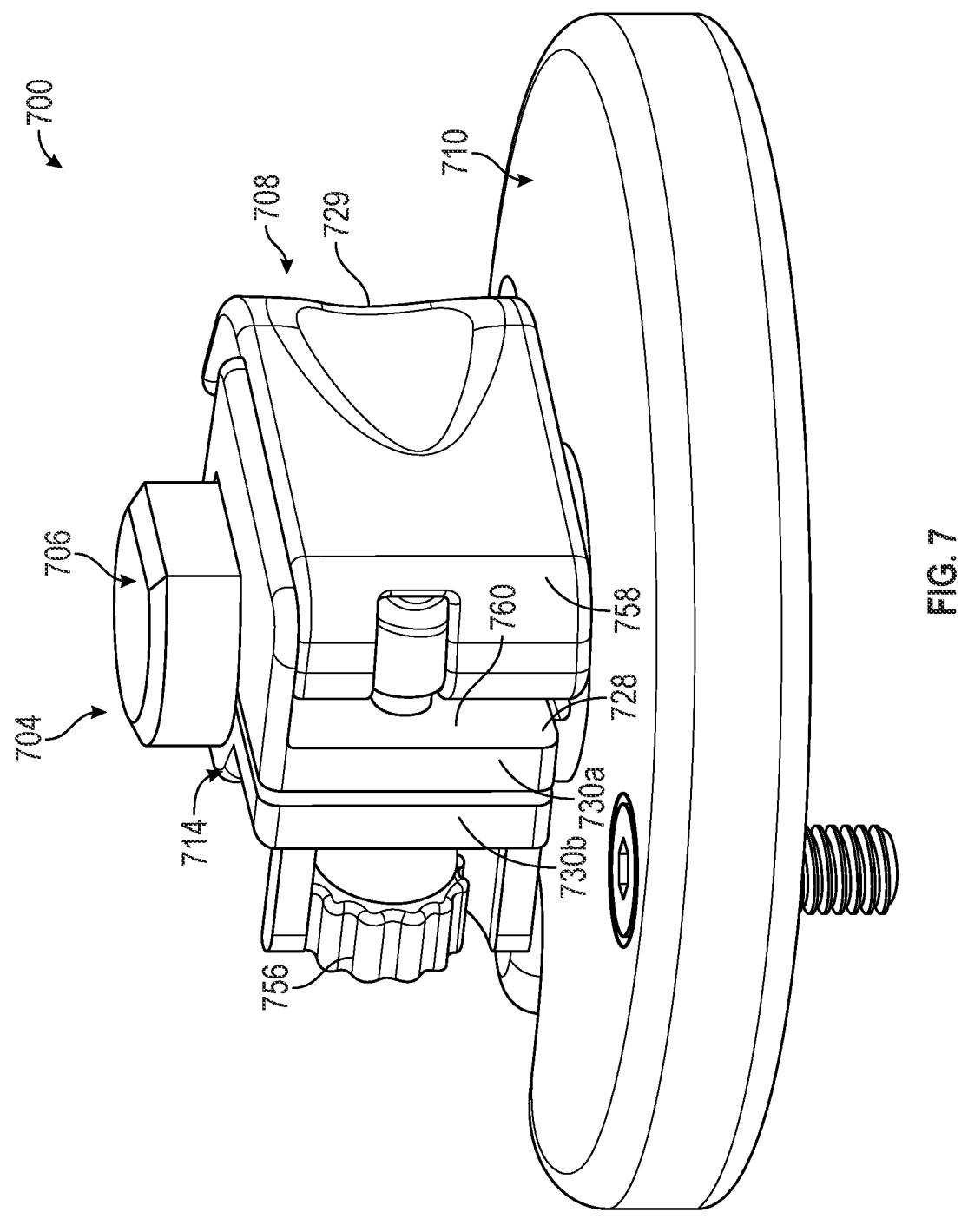
FIG. 7 illustrates an isometric view of a surgical tool and coupler for a robotic surgical system.

FIG. 7 illustrates an isometric view of a surgical tool 704 and coupler 702 for a robotic surgical system 700. The system 700 can be similar to the systems 200 of FIG. 2-5 or 600 of FIG. 6 where like numerals can represent like components; the system 700 can differ in actuator can be a cam-type feature. Any of the systems or couplers discussed above can be modified to include such features.

More specifically, an actuator 708 of the coupler 702 of the system 700 can include a fastener 728 including a knob 756. The fastener 728 can be connected to a handle 729 and can pass through flanges 730*a* and 730*b* of a collar 714. The knob 756 can be used to adjust a tightness of the collar 714 when the lever or handle 729 is in a closed position, as shown in FIG. 7.

The handle or lever 729 can include a cam surface 758 engageable with a surface 760 of the flange 730*a*. The cam surface 758 can engage with the surface 760 of the flange 730*a* during movement of the handle 729 between an open position and a closed position to allow a camming action between the flange 730*a* and the handle or lever 729 such as to move the flanges 730*a* and 730*b* towards each other when the handle 729 is moved to the closed position. The actuator 708 can thereby provide a quick and efficient means to open and close the collar 714 for quick and easy securing or removal of the tool 704 to the coupler 702.

Figure 8:
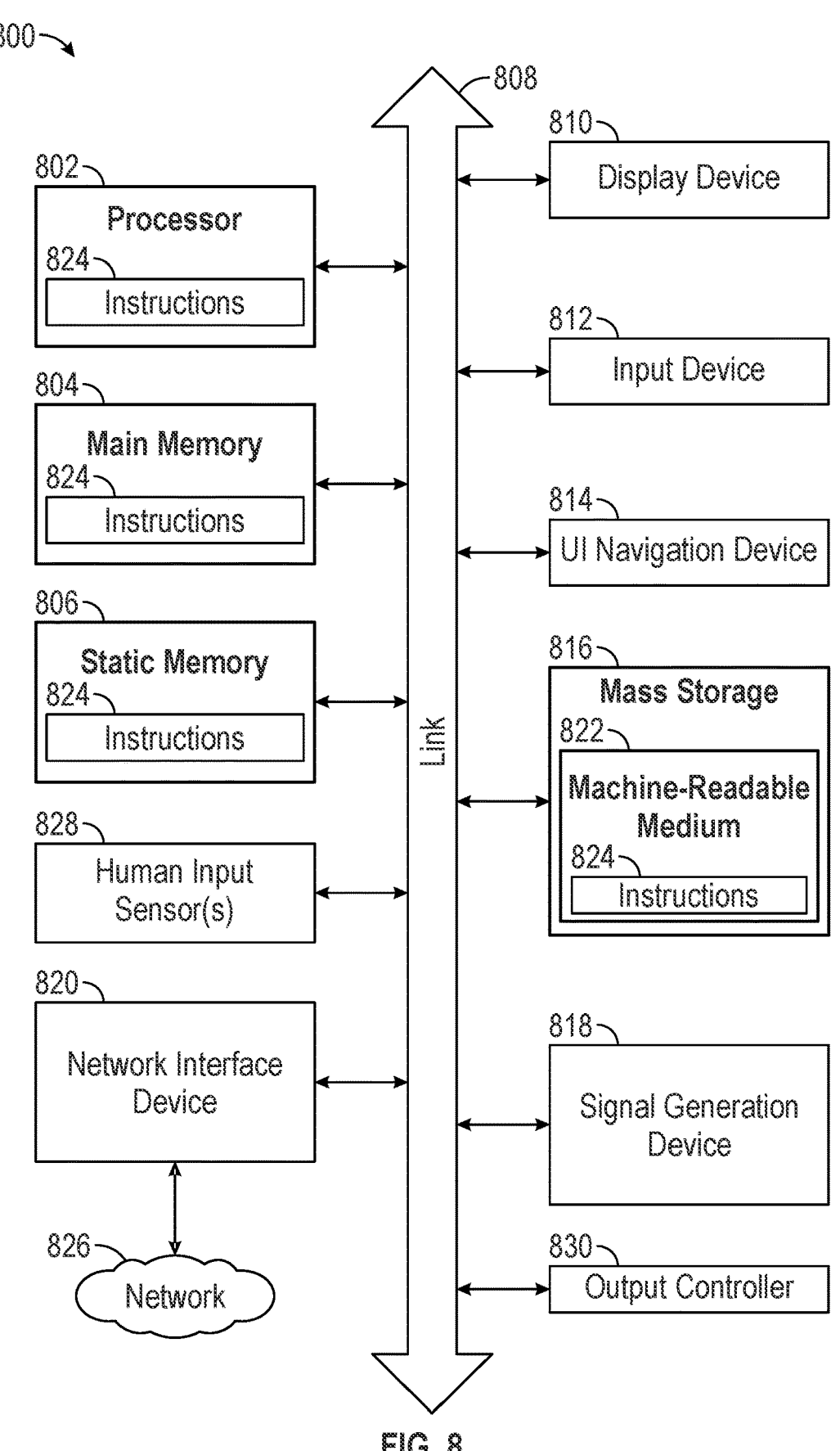
FIG. 8 illustrates a block diagram of an example machine upon which any one or more of the techniques discussed herein can be performed.

FIG. 8 illustrates a block diagram of an example machine 800 upon which any one or more of the techniques (e.g., methodologies) discussed herein may perform. Examples, as described herein, may include, or may operate by, logic or a number of components, or mechanisms in the machine 800. Circuitry (e.g., processing circuitry) is a collection of circuits implemented in tangible entities of the machine 800 that include hardware (e.g., simple circuits, gates, logic, etc.). Circuitry membership may be flexible over time. Circuitries include members that may, alone or in combination, perform specified operations when operating. In an example, hardware of the circuitry may be immutably designed to carry out a specific operation (e.g., hardwired). In an example, the hardware of the circuitry may include variably connected physical components (e.g., execution units, transistors, simple circuits, etc.) including a machine readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware e.g., the execution units or a loading mechanism) to create members of the circuitry in hardware via the variable connections to carry out portions of the specific operation when in operation. Accordingly, in an example, the machine readable medium elements are part of the circuitry or are communicatively coupled to the other components of the circuitry when the device is operating. In an example, any of the physical components may be used in more than one member of more than one circuitry. For example, under operation, execution units may be used in a first circuit of a first circuitry at one point in time and reused by a second circuit in the first circuitry, or by a third circuit in a second circuitry at a different time. Additional examples of these components with respect to the machine 800 follow.

In alternative embodiments, the machine 800 may operate as a standalone device or may be connected (e.g., networked) to other machines. In a networked deployment, the machine 800 may operate in the capacity of a server machine, a client machine, or both in server-client network environments. In an example, the machine 800 may act as a peer machine in peer-to-peer (P2P) (or other distributed) network environment. The machine 800 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

The machine (e.g., computer system) 800 may include a hardware processor 802 (e.g., a central processing unit (CPU), a graphics processing unit (GPU), a hardware processor core, or any combination thereof), a main memory 804, a static memory (e.g., memory or storage for firmware, microcode, a basic-input-output (BIOS), unified extensible firmware interface (UEFI), etc.) 806, and mass storage 808

(e.g., hard drive, tape drive, flash storage, or other block devices) some or all of which may communicate with each other via an interlink (e.g., bus) 830. The machine 800 may further include a display unit 810, an alphanumeric input device 812 (e.g., a keyboard), and a user interface (UI) navigation device 814 (e.g., a mouse). In an example, the display unit 810, input device 812 and UI navigation device 814 may be a touch screen display. The machine 800 may additionally include a storage device (e.g., drive unit) 808, a signal generation device 818 (e.g., a speaker), a network interface device 820, and one or more sensors 816, such as a global positioning system (GPS) sensor, compass, accelerometer, or other sensor. The machine 800 may include an output controller 828, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

Registers of the processor 802, the main memory 804, the static memory 806, or the mass storage 808 may be, or include, a machine readable medium 822 on which is stored one or more sets of data structures or instructions 824 (e.g., software) embodying or utilized by any one or more of the techniques or functions described herein. The instructions 824 may also reside, completely or at least partially, within any of registers of the processor 802, the main memory 804, the static memory 806, or the mass storage 808 during execution thereof by the machine 800. In an example, one or any combination of the hardware processor 802, the main memory 804, the static memory 806, or the mass storage 808 may constitute the machine readable media 822. While the machine readable medium 822 is illustrated as a single medium, the term "machine readable medium" may include a single medium or multiple media (e.g., a centralized or distributed database, and/or associated caches and servers) configured to store the one or more instructions 824.

The term "machine readable medium" may include any medium that is capable of storing, encoding, or carrying instructions for execution by the machine 800 and that cause the machine 800 to perform any one or more of the techniques of the present disclosure, or that is capable of storing, encoding or carrying data structures used by or associated with such instructions. Non-limiting machine readable medium examples may include solid-state memories, optical media, magnetic media, and signals (e.g., radio frequency signals, other photon based signals, sound signals, etc.). In an example, a non-transitory machine readable medium comprises a machine readable medium with a plurality of particles having invariant (e.g., rest) mass, and thus are compositions of matter. Accordingly, non-transitory machine-readable media are machine readable media that do not include transitory propagating signals. Specific examples of non-transitory machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 824 may be further transmitted or received over a communications network 826 using a transmission medium via the network interface device 820 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, the network interface device 820 may include one or more physical jacks (e.g., Ethernet, coaxial, or phone jacks) or one or more antennas to connect to the communications network 826. In an example, the network interface device 820 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 800, and includes digital or analog communications signals or other intangible medium to facilitate communication of such software. A transmission medium is a machine readable medium.

Notes and Examples

The following, non-limiting examples, detail certain aspects of the present subject matter to solve the challenges and provide the benefits discussed herein, among others.

Example 1 is a coupler for connecting one or more instruments to a robotic surgical arm, the coupler comprising: a base securable to the robotic surgical arm, the base comprising: a collar at least partially defining a stem bore extending at least partially into the base, the stem bore configured to receive a tool stem therein, the stem bore defining an axis; a retainer engageable with the stem to limit axial movement of the stem with respect to the collar; and an actuator connected to the collar and operable to move the collar between an open position and a closed position, the collar engaged with the stem in the closed position to secure the stem to the base and the robotic surgical arm.

In Example 2, the subject matter of Example 1 optionally includes wherein the retainer is configured to extend into the stem bore to engage a recess of the stem.

In Example 3, the subject matter of Example 2 optionally includes wherein the base defines a retainer bore intersecting the stem bore, the retainer bore configured to receive the retainer therein.

In Example 4, the subject matter of any one or more of Examples 1-3 optionally include wherein the collar includes a first flange and a second flange opposing the first flange, and wherein the actuator includes a threaded member extending through the first flange and threadably engaged with the second flange such that rotation of the actuator in a first direction causes the collar to move to the closed position and rotation of the actuator in a second direction, opposite the first direction, causes the collar to move to the open position.

In Example 5, the subject matter of any one or more of Examples 1-4 optionally include wherein the collar includes a fixed portion and a movable portion, the actuator operable to move the movable portion with respect to the fixed portion.

In Example 6, the subject matter of Example 5 optionally includes wherein the movable portion is cantilevered from the fixed portion.

In Example 7, the subject matter of any one or more of Examples 5-6 optionally include wherein the movable portion is separated from the base by a gap.

In Example 8, the subject matter of Example 7 optionally includes wherein the gap extends around at least a quarter of a circumference of the collar.

In Example 9, the subject matter of any one or more of Examples 1-8 optionally include wherein the stem bore has a D-shape to receive the stem having a complimentary D-shape to limit relative rotation of the stem with respect to the collar and the base.

In Example 10, the subject matter of any one or more of Examples 1-9 optionally include wherein the base includes a fastener bore extending therethrough to receive a screw therein to secure the base to the robotic surgical arm.

Example 11 is a robotic surgical arm assembly comprising: a tool stem; and a coupler securable to the robotic arm, the coupler comprising: a collar at least partially defining a stem bore configured to receive the tool stem therein, the stem bore defining an axis; a retainer engageable with the stem to limit axial movement of the stem with respect to the collar; and an actuator connected to the collar and operable to move the collar between an open position and a closed position, the collar engaged with the stem in the closed position to secure the stem to the coupler and the robotic surgical arm.

In Example 12, the subject matter of Example 11 optionally includes wherein the retainer is configured to extend into the stem bore to engage a recess of the stem.

In Example 13, the subject matter of Example 12 optionally includes wherein the coupler defines a retainer bore intersecting the stem bore, the retainer bore configured to receive the retainer therein.

Example 14, the subject matter of any one or more of Examples 11-13 optionally include wherein the collar includes a first flange and a second flange opposing the first flange, and wherein the actuator includes a threaded member extending through the first flange and threadably engaged with the second flange such that rotation of the actuator in a first direction causes the collar to move to the closed position and rotation of the actuator in a second direction, opposite the first direction, causes the collar to move to the open position.

In Example 15, the subject matter of any one or more of Examples 11-14 optionally include wherein the collar includes a fixed portion and a movable portion, the actuator operable to move the movable portion with respect to the fixed portion.

In Example 16, the subject matter of any one or more of Examples 11-15 optionally include wherein the movable portion is cantilevered from the fixed portion.

In Example 17, the subject matter of any one or more of Examples 11-16 optionally include wherein the movable portion is separated from a base of the coupler by a gap that extends around at least a quarter of a circumference of the collar.

Example 18 is a coupler for connecting one or more instruments to a robotic surgical arm, the coupler comprising: a base securable to the robotic surgical arm, the base comprising: a collar at least partially defining a stem bore extending at least partially into the base, the stem bore configured to receive a tool stem therein, the stem bore defining an axis; a plurality of retainers engageable with the stem to limit axial movement of the stem with respect to the collar; and an actuator connected to the collar and operable to move the collar between an open position and a closed position, the collar engaged with the stem in the closed position to secure the stein to the base and the robotic surgical arm.

In Example 19, the subject matter of Example 18 optionally includes wherein the plurality of retainers are configured to extend into the stem bore to engage a recess of the stem.

Example 20, the subject matter of Example 19 optionally includes wherein the base defines a plurality of retainer bores each intersecting the stem bore, each of the plurality of retainer bores configured to receive a retainer of the plurality of retainers therein.

In Example 21, the apparatuses or method of any one or any combination of Examples 1-20 can optionally be configured such that all elements or options recited are available to use or select from.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A coupler for connecting one or more instruments to a robotic surgical arm, the coupler comprising:
    a base securable to the robotic surgical arm, the base comprising:
        a collar at least partially defining a stem bore extending at least partially into the base, the stem bore configured to receive a tool stem therein, the stem bore defining an axis, the collar including a fixed portion and a movable portion cantilevered from the fixed portion;
        a retainer engageable with the tool stem to limit axial movement of the tool stem with respect to the collar; and
        an actuator connected to the collar and operable to move the collar between an open position and a closed position, the collar engageable with the tool stem in the closed position to secure the tool stem to the base and the robotic surgical arm, and the actuator operable to move the movable portion with respect to the fixed portion.

2. The coupler of claim 1, wherein the retainer is configured to extend into the stem bore to engage a recess of the tool stem.

3. The coupler of claim 2, wherein the base defines a retainer bore intersecting the stem bore, the retainer bore configured to receive the retainer therein.

4. The coupler of claim 1, wherein the collar includes a first flange and a second flange opposing the first flange, and wherein the actuator includes a threaded member extending through the first flange and threadably engaged with the second flange such that rotation of the actuator in a first direction causes the collar to move to the closed position and rotation of the actuator in a second direction, opposite the first direction, causes the collar to move to the open position.

5. The coupler of claim 1, wherein the movable portion is separated from the base by a gap.

6. The coupler of claim 5, wherein the gap extends around at least a quarter of a circumference of the collar.

7. The coupler of claim 1, wherein the stem bore has a D-shape to receive the tool stem having a complimentary D-shape to limit relative rotation of the tool stem with respect to the collar and the base.

8. The coupler of claim 1, wherein the base includes a fastener bore extending therethrough to receive a screw therein to secure the base to the robotic surgical arm.

9. A robotic surgical arm assembly including a robotic surgical arm, the robotic surgical arm assembly comprising:
    a tool stem; and
    a coupler securable to the robotic surgical arm, the coupler comprising:
        a collar at least partially defining a stem bore configured to receive the tool stem therein, the stem bore defining an axis, the collar including a fixed portion and a movable portion cantilevered from the fixed portion;
        a retainer engageable with the tool stem to limit axial movement of the tool stem with respect to the collar; and
        an actuator connected to the collar and operable to move the collar between an open position and a closed position, the collar engaged with the tool stem in the closed position to secure the tool stem to the coupler and the robotic surgical arm, and the actuator operable to move the movable portion with respect to the fixed portion.

10. The assembly of claim 9, wherein the retainer is configured to extend into the stem bore to engage a recess of the tool stem.

11. The assembly of claim 10, wherein the coupler defines a retainer bore intersecting the stem bore, the retainer threadably securable to the retainer bore.

12. The assembly of claim 9, wherein the collar includes a first flange and a second flange opposing the first flange, and wherein the actuator includes a threaded member extending through the first flange and threadably engaged with the second flange such that rotation of the actuator in a first direction causes the collar to move to the closed position and rotation of the actuator in a second direction, opposite the first direction, causes the collar to move to the open position.

13. The coupler of claim 9, wherein the movable portion is separated from a base of the coupler by a gap that extends around at least a quarter of a circumference of the collar.

14. A coupler for connecting one or more instruments to a robotic surgical arm, the coupler comprising:

a base securable to the robotic surgical arm, the base comprising:

a collar at least partially defining a stem bore extending at least partially into the base, the stem bore configured to receive a tool stem therein, the stem bore defining an axis, the collar including a fixed portion and a movable portion;

a plurality of retainers engageable with the tool stem to limit axial movement of the tool stem with respect to the collar; and an actuator connected to the collar and operable to move the collar between an open position and a closed position, the collar engageable with the tool stem in the closed position to secure the tool stem to the base and the robotic surgical arm, and the actuator operable to move the movable portion with respect to the fixed portion.

15. The coupler of claim 14, wherein the plurality of retainers are configured to extend into the stem bore to engage a recess of the tool stem.

16. The coupler of claim 15, wherein the base defines a plurality of retainer bores each intersecting the stem bore, each of the plurality of retainer bores configured to receive a retainer of the plurality of retainers therein.

\*  \*  \*  \*  \*